United States Patent
Kurz

Patent Number: 6,149,664
Date of Patent: *Nov. 21, 2000

[54] SHAPE MEMORY PUSHER INTRODUCER FOR VASOOCCLUSIVE DEVICES

[75] Inventor: Daniel R. Kurz, Sunnyvale, Calif.

[73] Assignee: Micrus Corporation, Mountain View, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/141,166

[22] Filed: Aug. 27, 1998

[51] Int. Cl.$^7$ .................................................. A61M 29/00

[52] U.S. Cl. ......................................... 606/194; 606/108

[58] Field of Search .................................... 606/108, 191, 606/194, 200, 151

[56] References Cited

U.S. PATENT DOCUMENTS

| | | |
|---|---|---|
| Re. 32,348 | 2/1987 | Pevsner . |
| 1,341,052 | 5/1920 | Gale . |
| 1,667,730 | 5/1928 | Green . |
| 2,078,182 | 4/1937 | MacFarland . |
| 2,549,335 | 4/1951 | Rahthus . |
| 3,334,629 | 8/1967 | Cohn . |

(List continued on next page.)

FOREIGN PATENT DOCUMENTS

| | | |
|---|---|---|
| 0 183372 A1 | 6/1986 | European Pat. Off. . |
| 0 382014 A1 | 8/1990 | European Pat. Off. . |
| 0 717 961 A1 | 6/1996 | European Pat. Off. . |
| 592182 | 7/1925 | France . |
| 4102550 A1 | 8/1991 | Germany . |
| 2 066 839 | 7/1981 | United Kingdom . |
| 92/14408 | 3/1992 | WIPO . |
| 94/16629 | 4/1994 | WIPO . |
| 96/18343 | 2/1996 | WIPO . |
| 97/01368 | 1/1997 | WIPO . |
| 98/02100 | 1/1998 | WIPO . |

OTHER PUBLICATIONS

Christos A. Athanasoulis, M.D. The New England Journal of Medicine, May 15, 1980 "Therapeutic Applications of Angiography" pp. 1117–1125 (1 of 2).

Christos A. Athanasoulis, M.D. The New England Journal of Medicine, May 22, 1980 "Therapeutic Applications of Angiography" pp. 1174–1179 (2 of 2).

Alex Berenstein, M.D. and Irvin I. Kricheff, M.D. "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of the Head, Neck, and Spine" Sep., 1975; pp. 275–287.

Stephen L. Kaufman, M.D. et al. Investigative Radiology, May–Jun. 1978 "Transcatheter Embolization with Microfibrillar Collagen in Swine"; pp. 200–204.

(List continued on next page.)

Primary Examiner—Michael Buiz
Assistant Examiner—Kevin Truong
Attorney, Agent, or Firm—Fulwider Patton Lee & Utecht, LLP

[57] ABSTRACT

An introducer for retaining an implant placed within an implant delivery device having a pusher for displacing the implant includes a tube and a clamp. The interior of the tube defines a passage for guiding the movement of the pusher. The clamp is made of a shape memory material disposed in the passage about the pusher. The clamp is normally operative to grip the pusher to hold it in position relative to the tube and further operative in response to an elevated temperature to release the pusher for movement relative to the tube. The clamp may be formed integrally with the tube and may comprise at least one crimp or an annular ring surrounding the tube. The tube is tapered to be narrower at its distal end and may be formed of a shaped memory polymer material.

20 Claims, 2 Drawing Sheets

U.S. PATENT DOCUMENTS

| | | |
|---|---|---|
| 3,649,224 | 3/1972 | Anderson et al. . |
| 3,868,956 | 3/1975 | Alfidi et al. . |
| 4,327,734 | 5/1982 | White, Jr. . |
| 4,341,218 | 7/1982 | äU . |
| 4,402,319 | 9/1983 | Handa et al. . |
| 4,441,495 | 4/1984 | Hicswa . |
| 4,494,531 | 1/1985 | Gianturco . |
| 4,512,338 | 4/1985 | Balko et al. . |
| 4,545,367 | 10/1985 | Tucci . |
| 4,638,803 | 1/1987 | Rand . |
| 4,655,771 | 4/1987 | Wallsten . |
| 4,718,907 | 1/1988 | Karwoski et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,884,579 | 12/1989 | Engelson . |
| 4,904,048 | 2/1990 | Sogawa et al. . |
| 4,950,258 | 8/1990 | Kawai et al. . |
| 4,954,126 | 9/1990 | Wallsten . |
| 4,957,479 | 9/1990 | Roemer . |
| 4,957,501 | 9/1990 | Lahille et al. . |
| 4,969,890 | 11/1990 | Sugita et al. . |
| 4,990,155 | 2/1991 | Wilkoff . |
| 4,994,069 | 2/1991 | Ritchart et al. . |
| 5,026,377 | 6/1991 | Burton et al. . |
| 5,037,427 | 8/1991 | Harada et al. . |
| 5,041,084 | 8/1991 | DeVries et al. . |
| 5,055,101 | 10/1991 | McCoy . |
| 5,064,435 | 11/1991 | Porter . |
| 5,071,407 | 12/1991 | Termin et al. . |
| 5,089,005 | 2/1992 | Harada . |
| 5,104,404 | 4/1992 | Wolff . |
| 5,108,407 | 4/1992 | Geremia et al. . |
| 5,109,867 | 5/1992 | Twyford, Jr. . |
| 5,122,136 | 6/1992 | Guglielmi et al. . |
| 5,133,731 | 7/1992 | Butler et al. . |
| 5,133,732 | 7/1992 | Wiktor . |
| 5,141,502 | 8/1992 | Macaluso, Jr. . |
| 5,147,370 | 9/1992 | McNamara et al. . |
| 5,151,105 | 9/1992 | Kwan-Gett . |
| 5,151,152 | 9/1992 | Kaeufe et al. . |
| 5,160,341 | 11/1992 | Brenneman et al. . |
| 5,170,801 | 12/1992 | Casper et al. . |
| 5,176,625 | 1/1993 | Brisson . |
| 5,176,661 | 1/1993 | Evard et al. . |
| 5,183,085 | 2/1993 | Timmermans . |
| 5,186,992 | 2/1993 | Kite, III . |
| 5,203,772 | 4/1993 | Hammerslag et al. . |
| 5,217,484 | 6/1993 | Marks . |
| 5,222,969 | 6/1993 | Gillis . |
| 5,226,911 | 7/1993 | Chee et al. . |
| 5,228,453 | 7/1993 | Sepetka . |
| 5,234,456 | 8/1993 | Silvestrini . |
| 5,250,071 | 10/1993 | Palermo . |
| 5,304,119 | 4/1994 | Balaban et al. ........................ 606/108 |
| 5,304,194 | 4/1994 | Chee et al. . |
| 5,312,152 | 5/1994 | Woekbkenberg, Jr. et al. . |
| 5,312,415 | 5/1994 | Palermo . |
| 5,336,205 | 8/1994 | Zenzen et al. . |
| 5,342,387 | 8/1994 | Summers . |
| 5,350,397 | 9/1994 | Palermo et al. . |
| 5,354,295 | 10/1994 | Guglielmi et al. . |
| 5,382,259 | 1/1995 | Phelps et al. . |
| 5,411,475 | 5/1995 | Atala et al. . |
| 5,423,829 | 6/1995 | Pham et al. . |
| 5,441,516 | 8/1995 | Wang et al. . |
| 5,443,478 | 8/1995 | Purdy . |
| 5,514,176 | 5/1996 | Bosley, Jr. . |
| 5,522,836 | 6/1996 | Palermo . |
| 5,549,624 | 8/1996 | Mirigian et al. . |
| 5,562,641 | 10/1996 | Flomenblit et al. . |
| 5,569,245 | 10/1996 | Guglielmi et al. . |
| 5,578,074 | 11/1996 | Mirigian . |
| 5,582,619 | 12/1996 | Ken . |
| 5,607,445 | 3/1997 | Summers . |
| 5,624,461 | 4/1997 | Mariant . |
| 5,636,642 | 6/1997 | Palermo . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,564 | 7/1997 | Northrup et al. . |
| 5,649,949 | 7/1997 | Wallace et al. . |
| 5,653,691 | 8/1997 | Ruff et al. . |
| 5,666,968 | 9/1997 | Imran et al. . |
| 5,667,522 | 9/1997 | Flomenblit et al. . |
| 5,676,697 | 10/1997 | McDonald . |
| 5,690,643 | 11/1997 | Wijay . |
| 5,690,666 | 11/1997 | Berenstein et al. . |
| 5,690,671 | 11/1997 | McGurk et al. . |
| 5,693,086 | 12/1997 | Goicoechea et al. . |
| 5,695,111 | 12/1997 | Nanis et al. . |
| 5,722,989 | 3/1998 | Fitch et al. . |
| 5,725,546 | 3/1998 | Samson . |
| 5,746,769 | 5/1998 | Ton et al. . |
| 5,749,837 | 5/1998 | Palermo et al. . |
| 5,749,894 | 5/1998 | Engelson . |
| 5,814,062 | 9/1998 | Sepetka et al. . |
| 5,895,391 | 4/1999 | Farnholtz ........................ 606/108 |
| 5,944,733 | 8/1999 | Engelson . |

OTHER PUBLICATIONS

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975 "Selective Arterial Embolization for Control of Massive Upper Gastrointestinal Bleeding" pp. 119–126.

Glenn H. Roberson, et al., American Journal of Radiology, Oct. 1979 "Therapeutic Embolization of Juvenile Angiofibroma" pp. 657–663.

Sidney Wallace, M.D. et al., Cancer, Oct. 1979 "Arterial Occlusion of Pelvic Bone Tumors"; pp. 322–325 & 661–663.

"Mechanical Devices for Arterial Occlusion" by C. Gianturco, M.D., et al., Jul. 1975 pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occlusion of Experimental Arteriovenous Fistulas", by James H. Anderson, et al., Am. J. Roentgenol, Nov. 1977, pp. 795–798.

"'Mini' Gianturco Stainless Steel Coils for Transcatheter Vascular Occlusion" by James H. Anderson, et al., From the Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

SHAPE MEMORY PUSHER INTRODUCER FOR VASOOCCLUSIVE DEVICES

BACKGROUND OF THE INVENTION

1. Field of the Invention

This invention relates generally to the field of interventional medical devices, and more particularly concerns an introducer, for securely holding and remotely releasing a vasoocclusive implant at precise locations within the vasculature of a patient.

2. Description of Related Art

The medical community has long sought methods to treat aneurysms which, especially when located in the brain cause a grave threat to life. An aneurysm is a bulge or bubble which sometimes forms in a blood vessel. These aneurysms can leak or burst, often leading to instant death or paralysis. A previous, extremely invasive procedure for treating aneurysms located in a patient's brain involved cutting open the patient's skull to gain access to the aneurysm and then clamping it off to eliminate blood flow to the aneurysm. It can be appreciated that such procedures are extremely risky and require long recovery times.

More recently, the medical community discovered that by implanting a tiny foreign object, referred to herein as a vasoocclusive implant, into the aneurysm an occlusion naturally forms, blocking off blood flow to the aneurism and preventing rupture. The medical community also discovered that tiny helical coils defining narrow cylinders provide very effective vasoocclusive implants because of there ability to form random looped configurations within the aneurysm to effectively fill the aneurysm.

One problem which has surfaced in connection with this procedure is finding an effective way to release the vasoocclusive implant within the aneurism. The implant must be precisely positioned within the aneurism. An inadvertent release of such an implant into the patient's bloodstream could pose grave consequences.

One device which has been developed to release such a vasoocclusive implant involves affixing the implant to a connector using a heat releasable adhesive. The connector of this invention is heated by light energy transmitted through a fiber optic cable. The use of fiber optic cables has proven to be an effective and minimally invasive technique for deploying such implants. This method provides an effective means of introducing such an implant. However, such a method suffers a shortcoming in that some amount of adhesive is released into the blood stream.

Another method which has been employed to release an vasoocclusive implant involves setting up an electrolytic reaction to corrode a sacrificial link. In this procedure, an electrical charge is conducted through the catheter to the implant. The base of the implant has a small cross section, which eventually corrodes to the point of breakage to release the implant. This procedure has also proven effective for releasing an implant. However, the process of releasing the implant can take quite a long time, eg. 4 minutes to 1 hour, and since a given operation can often require several implants the time required can be extensive, thus increasing the risk to the patient. In addition, it is not clear what effect such an electrical current, conducted to the patient's brain, might have on the patient. Furthermore, this procedure also emits byproducts of the electrolytic reaction directly into the patient's bloodstream.

Still other procedures have been developed which take advantage of the property exhibited by certain materials to, upon being deformed and later raised to a given temperature, return to their pre-deformed shape. One such device employs a connector in the form of a bent wire. The connector, disposed within the center of the implant, is bent to engage the inner walls of the implant to hold the implant in place. When the implant is to be released, the connector is heated and, upon reaching is transition temperature, returns to an unbent shape. At this point the connector can be pulled out from the implant, leaving the implant behind. While such a device can effectively release engagement of the implant, it does not eject the implant. The implant remains disposed about the wire. There is always the chance that upon removing the wire from the center of the implant, the surgeon may inadvertently move the implant, which must be precisely located.

In still another method of inserting a vasoocclusive implant, a hollow catheter is inserted into the vascular system of the patient with a guide wire held within the lumen of the catheter. Once the catheter is properly in place, the guide wire is removed from the catheter and the implant inserted, followed by a pusher wire. The pusher wire has an end formed with screw threads which engages the inside of the implant to securely hold the implant onto the end of the pusher wire. The pusher wire is then used to push the implant through the catheter to the desired site in the vein. Once the implant is in place in the vein, the pusher wire is twisted to unscrew it from the implant. While this procedure provides an effective means of placing the implant and can securely hold the implant until it is precisely located, it also has certain limitations. Removal of the guide wire and insertion of the pusher wire through the entire length of the catheter is time consuming, and any fluid or air disposed within the catheter will be flushed into the patient's bloodstream while the implant and pusher wire are fed through the catheter. In addition, the process of unscrewing the pusher wire from the implant can move the implant, leading an improperly placed implant.

Thus there remains a need for a device which can quickly eject an implant at a precise location within a patients vasculature. Such a device would preferably take advantage of the benefits provided by fiber optic technology for activation of a release mechanism. Also such a device would be capable of releasing the implant upon demand by the operator, without introducing extraneous matter or an electrical charge into the patient.

SUMMARY OF THE INVENTION

Briefly, and in general terms, the present invention provides a device for introducing a vasoocclusive implant at a precise location within a patients vasculature. The device comprises an introducer in the form of a hollow tapered tube. The introducer is formed of a shape memory material and is sized to contain a vasoocclusive implant, and a pusher which can slide within the introducer to eject the implant. The introducer clamps the pusher in place until the implant is to be ejected. When the implant is to be ejected the introducer is heated. Upon reaching the aforementioned predetermined temperature, the introducer operates to release the pusher so that it can move within the introducer to eject the implant.

A shape memory polymer exhibits the property that, when raised above its glass transition temperature, deformed and then cooled, it maintains its pre-deformed shape until subsequently heated again to its glass transition temperature at which time it returns to its pre-deformed shape. The introducer in which the implant and pusher are housed is constructed of such a shape memory polymer. Deforming the introducer radially inwardly while it is above its glass transition temperature, forms a clamp to hold the pusher in place within the introducer. Taking advantage of the shape memory property of the material, when the implant is to be released the introducer is heated to its glass transition temperature. This causes the introducer to return to its pre-deformed shape, thereby removing the clamp and allowing the pusher to move axially within the introducer to release the implant.

In a presently preferred embodiment a fiber optic cable is used to guide the implantation device through the patient's vascular system as well as to supply light energy to heat the introducer to release the implant. A fiber optic cable has the advantage of being very fine to fit withing the narrow venous pathways in the brain. In addition a fiber optic cable can transmit energy to the introducer without heating the tissue through which the fiber is routed.

In another preferred embodiment, the pusher is biased toward the distal extremity of the introducer so that when the clamp is released, the pusher automatically forces the implant out of the end of the introducer. This device has the advantage of simplicity and allows a very narrow cable to be used to guide the introducer into place within the patient's vascular system.

In another embodiment, the fiber optic cable is housed within a sheath. With the cable attached to the pusher and the sheath attached to the introducer, manipulation of the cable relative to the introducer can cause movement of the pusher within the introducer to eject the implant from the introducer. This embodiment has the advantage of providing the surgeon with greater control over the operation of pusher when releasing an implant. The fiber optic cable can be provided with a jacket to provide added stiffness as needed to manipulate the pusher.

These and other features and advantages of the invention will become apparent from the following detailed description, taken in conjunction with the accompanying drawing, which illustrate by way of example the features of the invention.

DETAILED DESCRIPTION OF THE PREFERRED EMBODIMENTS

Figure 1:
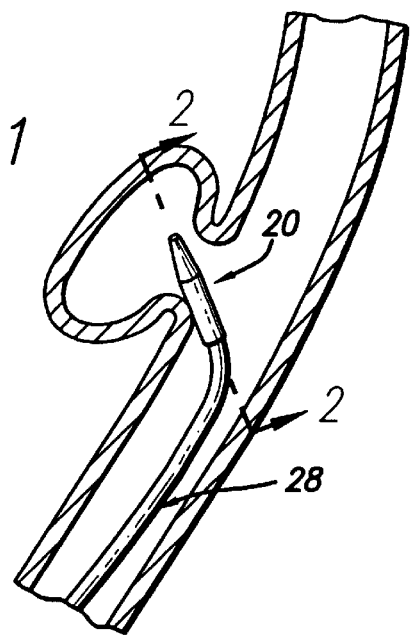
FIG. 1 is a fragmentary cross-sectional view of the device of the present invention being inserted into an aneurysm.
Figure 2:
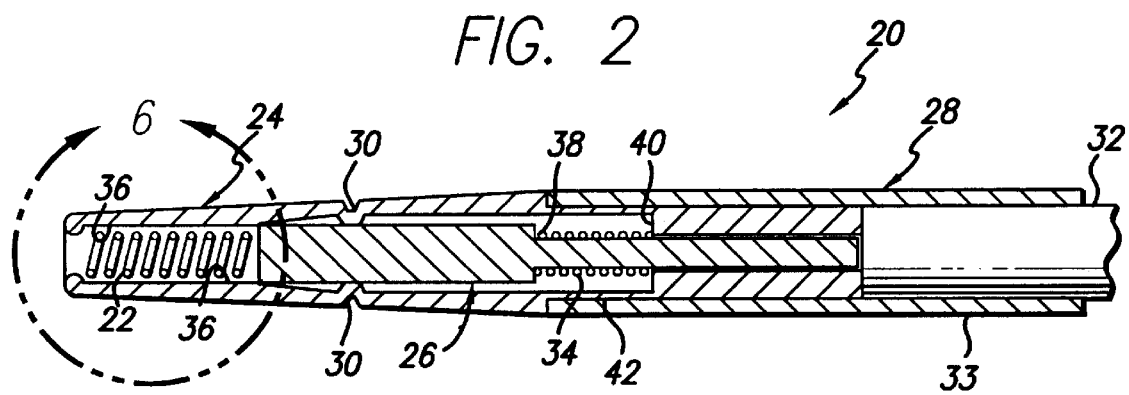
FIG. 2 is a cross sectional view, taken along line 2—2 in FIG. 1, shown in enlarged scale and rotated 75 degrees counterclockwise.

As shown in the drawings, which are provided for purposes of illustration and not by way of limitation, the present invention, as illustrated in FIGS. 1 & 2, is embodied in a system, generally designated 20, capable of inserting an implant 22 within the vascular system of a patient. The device employs an introducer, generally designated 24, and a pusher, generally designated 26, contained within the introducer, to eject the implant once it is precisely located within the vasculature of the patient. The introducer 24 is guided into position by a cable, generally designated 28.

With reference to FIG. 1, the introducer 24 of the present invention is in the form of a narrow, hollow, tapered tube having proximal and distal ends and having a smaller diameter at its distal end than at its proximal end. The taper allows the introducer 24 to be more easily guided within the vascular system and provides greater flexibility at its distal end than at its proximal end to facilitating bending the introducer through the tortuous bends of the vascular system. The introducer 24 includes a through extending bore 36, extending from its distal end to its proximal end. The bore contains both the implant 22 and the pusher 26.

Figure 3:
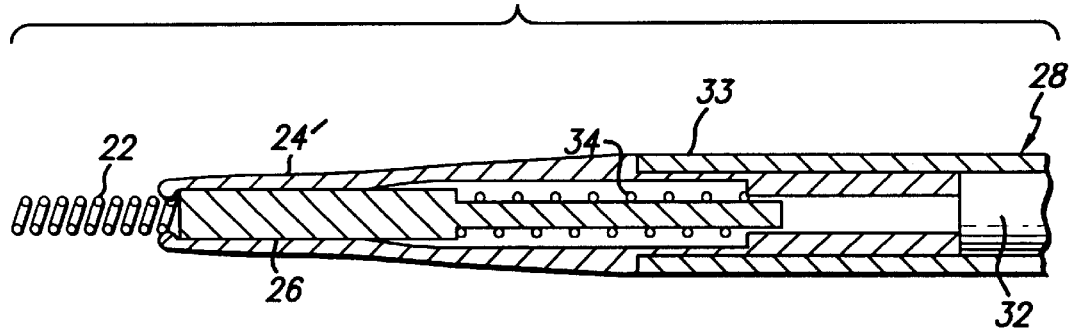
FIG. 3 is a cross sectional view, similar to FIG. 2, showing the introducer in an unclamped configuration with the implant being ejected.

The introducer 24 is constructed of a shape memory polymer having the advantage that when heated to its glass transition temperature and subsequently deformed and then cooled, it maintains its deformed shape until again heated to its glass transition temperature. The introducer 24 includes a clamp 30 formed on the introducer while it is above its transition temperature. The clamp 30 can be of various shapes, and by way of example can be formed as crimps as illustrated in FIG. 2 or as an annular ring. The clamps 30 hold the pusher 26 in position within the introducer 24 until the implant 22 is to be released. When the device 20 is properly positioned in the patient's vasculature and the implant 22 is ready to be released, heating the introducer 24 to its transition temperature causes the introducer to return to its original unclamped configuration as illustrated in FIG. 3. With the introducer 24' shaped as it was previous to when the clamps 30 (FIG. 2) were formed, the pusher 26 is free to move axially within the bore 36.

Figure 5:
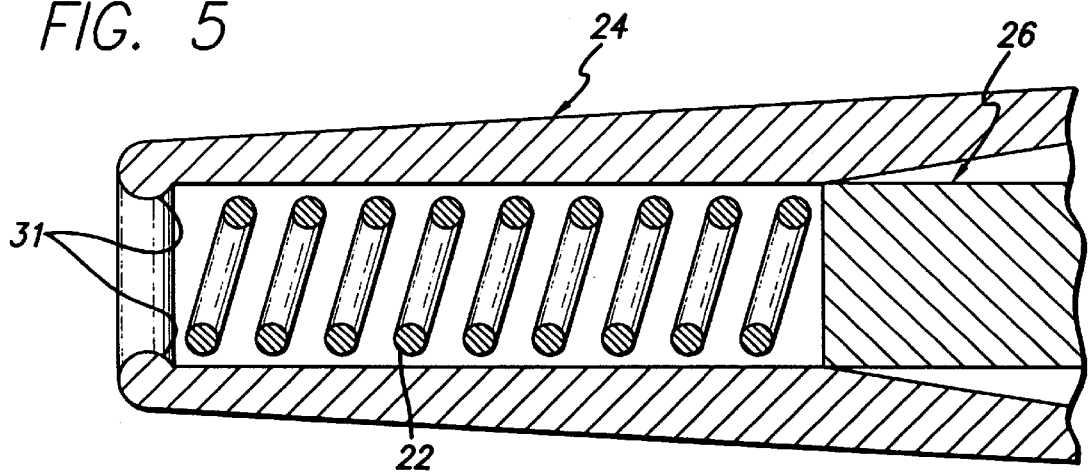
FIG. 5 is a fragmentary view, in enlarged scale, taken from circle 6 in FIG. 2.

With reference to FIG. 5, the distal end of the introducer 24 has a reduced inner diameter forming a stop 31 having a sufficiently large diameter to allow passage of the implant 22 therethrough, but being small enough to prevent the pusher 26 from coming out of the introducer.

Referring to FIG. 2, in a preferred embodiment of the invention, the cable 28 has at its core an optical fiber 32 which is surrounded by a jacket 33. The optical fiber 32 provides a conduit for the transmission of light energy to heat the pusher 26 and introducer 24. The jacket 33 provides the strength and flexibility to allow the cable 28 be fed through the vasculature. The cable terminates at its proximal end at a light source (not shown) such as a laser, and connects at its distal end to the introducer 24 through the pusher 26.

The pusher 26, is generally in the form of a rod having proximal and distal ends. The proximal end of the rod terminates near the distal termination of the fiber 32 of the cable 28 so that light energy transmitted through the cable can be imparted to the pusher 26 to heat the pusher. The thermal energy from the pusher 26 then conducts to the introducer 24 to heat the introducer.

In a preferred embodiment of the invention, a coil spring 34, located at the proximal end of the pusher 26, biases the pusher in the distal direction. While it will be apparent to one skilled in the art that other biasing mechanisms could also be employed, a coil spring is preferred because of its simplicity and its ability to impart an axial force to the pusher 26. The pusher 26 in this embodiment has a reduced cross section at its proximal end defining a pusher shoulder 38 against which the distal end of the spring 34 seats. Likewise, the proximal end of the bore 36 has a reduced diameter forming an introducer shoulder 40 against which the proximal end of the spring 34 seats. Although the spring 34 biases the pusher 26 in the distal direction, the pusher is held fixedly in the proximal position by the clamps 30 which bind against the pusher.

The diameter of the through extending bore 36 at the proximal end of the introducer 24 is sufficiently small to contain the spring 34, yet is large enough to allow passage of the proximal end of the pusher 26 therethrough. The exterior of the introducer 24 includes at its proximal end a reduced diameter portion forming an annular notch 42, extending through the proximal end of the introducer, over which the jacket 33 of the cable 28 fits. In this way the cable 28 can be securely attached to the introducer 24 while providing a flush surface at the juncture of the introducer and cable to promote the smooth passage of the device 20 through the patient's vascular system, avoiding tissue damage.

Figure 4:
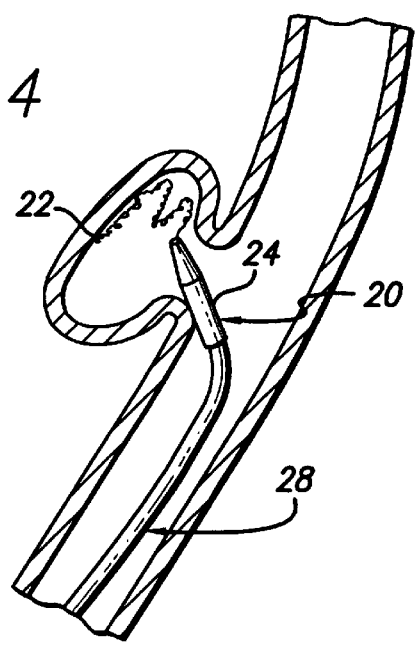
FIG. 4 is a fragmentary cross-sectional view of the device, similar to FIG. 1, of the present invention being inserted into an aneurysm with an implant being ejected and filling the aneurysm.

The introducer 24 contains the implant 22 within its bore 36 at its distal end opposite the spring 34. The implant 22 abuts the pusher 26 so that axial movement of the pusher in the distal direction, forces the implant out of the distal end of the introducer. The implant can be of many configurations as required by the particular application, but preferably forms a cylindrical helix. Experience has shown that a cylindrical helix provides both the strength and flexibility necessary to allow the implant to be forced into an aneurysm while allowing the implant to bend into various looped configuration to fill the aneurysm as illustrated in FIG. 4.

To construct the device 20 of this embodiment of the invention the introducer 24 is first molded of a shape memory polymer without a clamp 30. The cable 28 is then attached to the proximal end of the introducer 24 with the jacket 33 fitting onto the notch 42 on the introducer. The jacket 28 can be constructed by placing a layer of polymeric heat shrink tubing such as polyethylene terephthalate over the fiber 32 and over the annular notch 42. Each layer of heat shrink tubing is shrunk onto the fiber using a heat gun to heat the tubing to approximately 650° F., starting at one end and moving the heat gun at approximately three inches per second along the axis of the cable. The proximal end of the cable can then be connected to the light source.

The coil spring 34 is then inserted into the bore 36 from the distal end of the introducer 24. With the spring resting upon the introducer shoulder 40, the pusher 26 is inserted into the distal end of the introducer 24 so that the distal end of the spring rests upon the pusher shoulder 38. The stop 31 (FIG. 5) is sufficiently elastic to allow passage of the pusher 26 when forced into the introducer 24, while preventing the pusher from coming out of the introducer upon deployment of the implant. The pusher 26 is forced further in the proximal direction within the introducer to compress the spring 34. With the pusher 26 held in this position, the clamp 30 is formed by heating the introducer 24 to its glass transition temperature and then radially deforming the introducer to form crimps or an annular ring to grip the pusher 26 and thereby hold it in place within the introducer. The introducer 24 is then cooled. The vasoocclusive implant 22 is placed into the distal end of the bore of the introducer 24 to be securely held therein. So long as the introducer 24 remains below its glass transition temperature, the clamp 30 holds the pusher 26 in its proximal position in the bore with the spring 34 compressed. However, once the introducer 24 is heated to its transition temperature, the introducer returns to its pre-deformed configuration. The clamp 30 releases, allowing the spring 34 to force the pusher 26 in the distal direction forcing the vasoocclusive implant 22 out of the distal end of the introducer 24.

Figure 6:
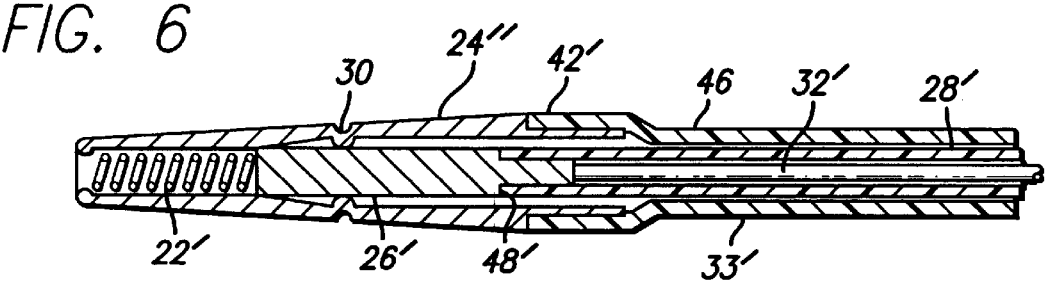
FIG. 6 is a view similar to FIG. 2, showing an alternate embodiment of the invention.

With reference to FIG. 6, in an alternate embodiment of the invention, the cable generally referred to as 28' is slidably encased within a sheath 46 which attaches at its distal end to the proximal end of the introducer 24". The distal end of the cable 28 attaches to the proximal end of the pusher 26'. The proximal end of the pusher 26 has a reduced diameter defining an annular pusher notch 48' on which the jacket 33' of the cable 28' tightly fits. Similarly, the proximal end of the introducer 24 forms an annular introducer notch 42' over which the sheath 46 tightly fits. This embodiment does not employ a spring to bias the pusher. Instead, manipulation of the cable 28' within the sheath 46 causes movement of the pusher 26' relative to the introducer 24".

To construct this embodiment, a cable 28' is first constructed similar to the previous preferred embodiment, however the jacket 33' is shrunk onto the annular pusher notch 48' with the distal end of the optical fiber 32' terminating at the proximal end of the pusher 26". The introducer 24" is then slid over the cable 28', starting at the proximal end of the cable, until the pusher 26' is enclosed sufficiently deep within the bore to provide a space in the distal end of the bore to hold the implant 22. The introducer 24" is then heated to its transition temperature as in the previous embodiment and a clamp 30 formed thereon to hold the pusher in place within the bore. The sheath 46 is then slipped over the cable 28', starting at the proximal end of the cable, until the distal end of the sheath fits over and affixes to the introducer notch 42'. The proximal end of the cable 28' is then connected to light source.

From the forgoing it will be appreciated by those skilled in the art that present invention provides an effective mechanism for releasing a vasoocclusive implant. The device allows a surgeon to precisely control both the time and location of implantation, and does not introduce any other foreign matter, such as electrolytic byproducts or adhesive, into the patients vascular system. Ejecting the implant out of the end of the introducer precludes the possibility inadvertent movement of the implant when withdrawing the cable. In addition, implant can be very quickly released once the introducer is properly placed, reducing the risk of incorrectly inserting the implant and also reducing the risk to the patient by reducing surgery time.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. An introducer for retaining an implant placed with in an implant delivery device having a pusher for displacing said implant, said introducer comprising:

a tube, the interior of said tube defining a passage for guiding the movement of said pusher; and a clamp of shape memory material disposed in said passage about said pusher and normally operative to grip said pusher to hold it in position relative to said tube and further operative in response to an elevated temperature to release said pusher for movement relative to said tube.

2. The introducer of claim 1, wherein said clamp and tube are formed integrally.

3. The introducer of claim 2, wherein said clamp comprises at least one crimp.

4. The introducer of claim 2, wherein said clamp comprises an annular ring surrounding said tube.

5. The introducer of claim 1, wherein said tube is tapered to be narrower at its distal end.

6. The introducer of claim 1, wherein the shaped memory material is a polymer material.

7. A vasoocclusive implant delivery device, comprising:
   an introducer for insertion into a vascular system to dispose a distal end at an embolism site, said introducer formed with a wall defining a pusher passage
   an implant disposed in said distal end;
   a pusher housed in said introducer, adjacent said implant; and
   a clamp of shape memory material disposed in said passage about said pusher and normally operative to grip said pusher to hold it in position relative to said introducer and further operative in response to an elevated temperature to release said pusher for movement relative to said introducer.

8. The implant delivery device of claim 7, wherein said clamp is formed integrally with said wall.

9. The implant delivery device of claim 7, wherein said introducer is tapered to be narrower at its distal end.

10. The implant delivery device of claim 7, further comprising a fiber optic cable having proximal and distal ends, connected at said proximal end to a source of light energy and connected at said distal end to said introducer.

11. The implant delivery device of claim 10, wherein said clamp is heated by light energy transmitted by said fiber optic cable.

12. The implant delivery device of claim 7, wherein said clamp is heated with electrical energy.

13. The implant delivery device of claim 7, wherein said pusher is biased in said distal direction to force said implant out of said distal extremity upon said release of said clamp.

14. The implant delivery device of claim 13, further comprising a spring, biasing said pusher in said distal direction.

15. The implant delivery device of claim 7, further comprising:
   a sheath having a distal end and attached at said distal end to said introducer; and
   a fiber optical cable within said sheath, having proximal and distal ends, attached at said distal end to said pusher and operable at said proximal end to manipulate said pusher within said introducer when said clamp is in said released configuration.

16. The implant delivery device of claim 15, wherein said cable is slidable within said sheath.

17. The implant delivery device of claim 15, wherein said cable comprises:
   an optical fiber; and
   a jacket, encasing said fiber and slidable within said sheath.

18. A method of manufacturing a vasoocclusive implant delivery device, comprising the steps of:
   selecting an introducer, having a wall defining a pusher passage, said introducer constructed of a shape memory material having the property that when heated to a predetermined temperature, deformed and cooled it returns to its original undeformed shape upon subsequently being heated to said predetermined temperature;
   inserting a pusher into said passage;
   heating said introducer to said predetermined temperature;
   deforming said wall to create a clamp to grip said pusher to hold it in position; and
   cooling said introducer.

19. The method of claim 18, further comprising the steps of:
   attaching a distal end of a fiber optic cable to said pusher;
   fitting a sheath over said fiber optic cable; and
   attaching said sheath to said introducer.

20. The method of claim 18, further comprising the step of prior to inserting said pusher into said passage, inserting a spring into said introducer.

* * * * *

UNITED STATES PATENT AND TRADEMARK OFFICE
CERTIFICATE OF CORRECTION

PATENT NO.   : 6,149,664
DATED        : November 21, 2000
INVENTOR(S)  : Daniel R. Kurz Page 1 of 1

It is certified that error appears in the above-identified patent and that said Letters Patent is hereby corrected as shown below:

Column 7,
Line 9, claim 7, after "end", add -- of said introducer --.
Line 35, claim 13, page change "said distal direction", to read -- a distal direction --.
Line 36, claim 13, change See above. "extremity", to read -- end of said introducer --.
Line 36, claim 13, change "clamp", to read -- pusher --.
Column 8,
Line 3, claim 15, after "shaft,", add -- said cable --.
Line 4, claim 15, after "said distal end", add -- of said cable --.
Line 5, claim 15, after "proximal end", add -- of said cable --.
Line 7, claim 15, change "said released", to read -- a released --.
Line 12, claim 17, delete "an optical fiber; and ,".
Line 13, claim 17, change "fiber", to read -- cable --.

Signed and Sealed this

Twenty-third Day of October, 2001

Attest:

NICHOLAS P. GODICI
Attesting Officer      Acting Director of the United States Patent and Trademark Office